(12) United States Patent
Gardiner

(10) Patent No.: US 6,301,807 B1
(45) Date of Patent: Oct. 16, 2001

(54) REHABILITATIVE SHOE INSOLE DEVICE

(75) Inventor: Roy J. W. Gardiner, Mount Albert (CA)

(73) Assignee: Barefoot Science Technologies Inc., Vaughan (CA)

( * ) Notice: Subject to any disclaimer, the term of this patent is extended or adjusted under 35 U.S.C. 154(b) by 0 days.

(21) Appl. No.: 09/243,457

(22) Filed: Feb. 3, 1999

Related U.S. Application Data

(63) Continuation-in-part of application No. 08/994,500, filed on Dec. 24, 1997, now abandoned.

(51) Int. Cl.$^7$ ................. A61F 5/14; A43B 13/40
(52) U.S. Cl. .................. 36/155; 36/43; 36/44; 36/27; 36/158
(58) Field of Search .................. 36/43, 44, 27, 36/155, 158, 168, 173, 179

(56) References Cited

U.S. PATENT DOCUMENTS

| | | | |
|---|---|---|---|
| 788,469 | * | 4/1905 | Huether . |
| 1,136,443 | * | 4/1915 | Scholl . |
| 1,142,849 | * | 6/1915 | Scholl . |
| 1,378,398 | * | 5/1921 | Block . |
| 2,157,454 | * | 5/1939 | Keys . |
| 5,404,659 | * | 4/1995 | Burke et al. . |
| 5,438,768 | * | 8/1995 | Bauerfeind . |

FOREIGN PATENT DOCUMENTS

83595-A   12/1919   (CH) .

\* cited by examiner

*Primary Examiner*—Ted Kavanaugh
(74) *Attorney, Agent, or Firm*—Gowling Lafleur Henderson LLP

(57) ABSTRACT

An insole device configured to fit the profile of the human foot to promote proprioceptive stimulation of the golgi tendon organ. The midfoot section of the insole device has an asymmetric domed structure that is presented to the plantar aspect of the foot at a location found to be the anatomical apex of the foot's arch system. The asymmetric domed structure displays physical properties to catalyse muscle group balancing by using the body's proprioceptive feedback mechanisms. The asymmetric domed structure displays physical properties such that it does not provide functional bracing or support to the plantar aspect of the foot. The net result will be a more structurally sound foot capable of more energy efficient and less injury inducing use. The plantar aspect of the insole or midsole device is characterized by a dominant cavity having the ability to receive and interchange the biofeedback catalyst and the many forms therefore, as well as being characterized by provisions to ensure proper and permanent placement of the catalyst.

15 Claims, 8 Drawing Sheets

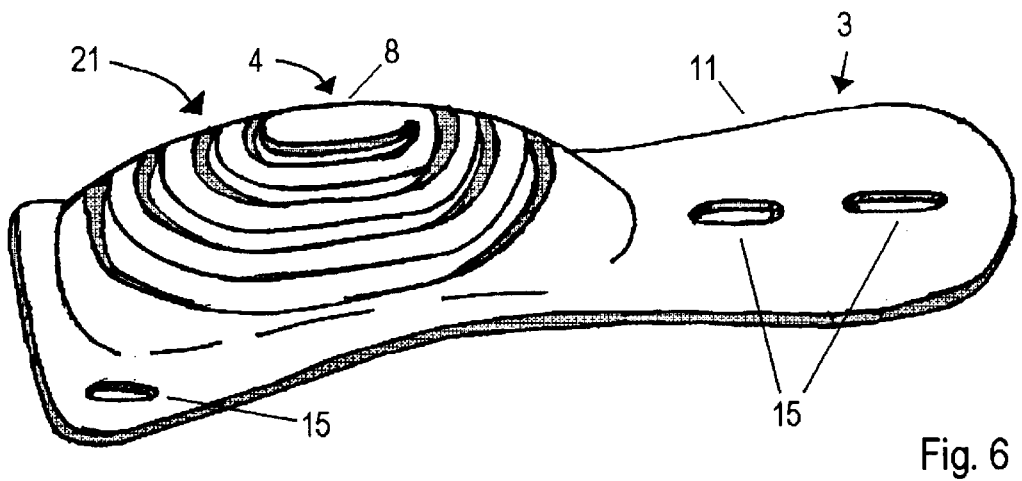
Fig. 6
Fig. 7
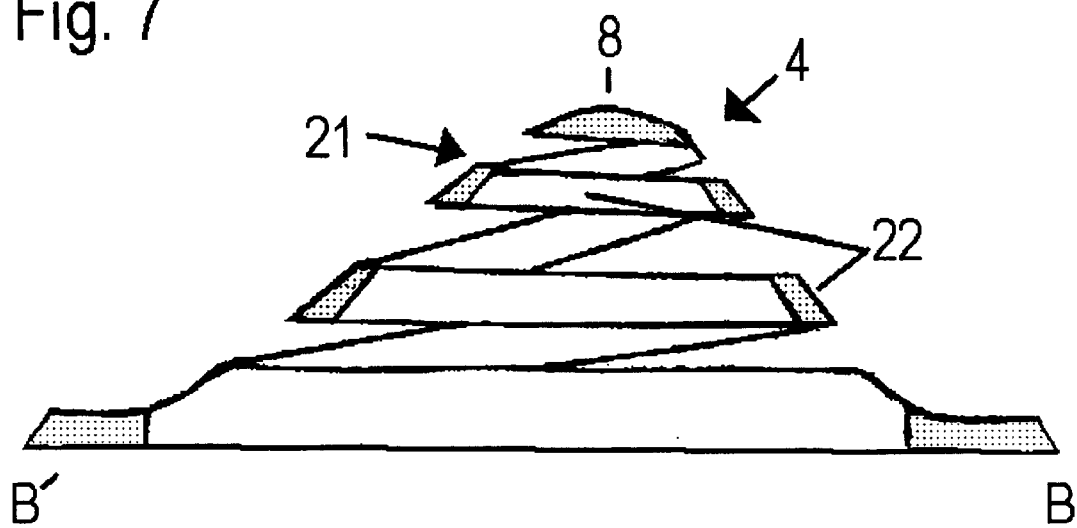
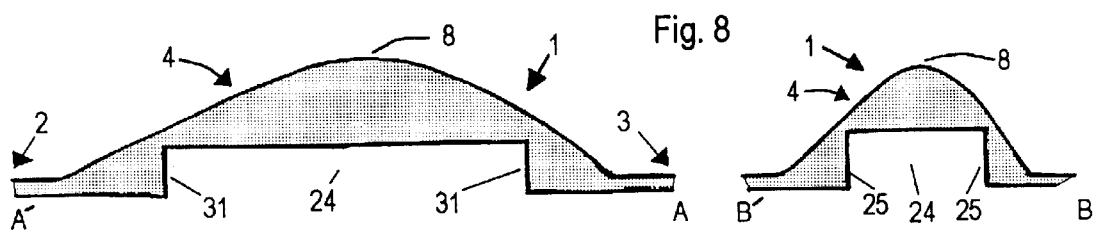
Fig. 8

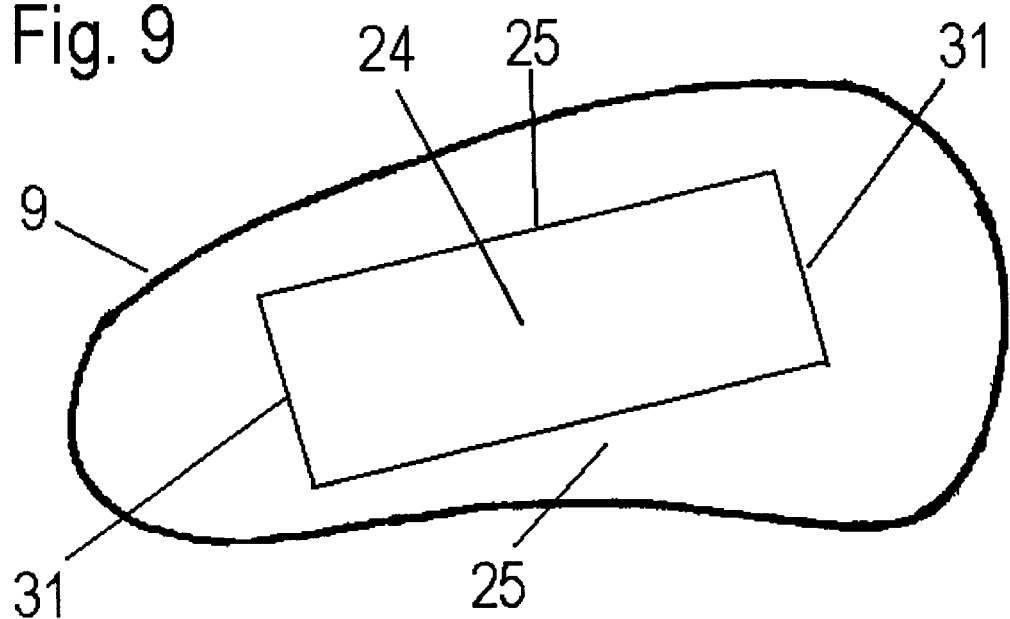
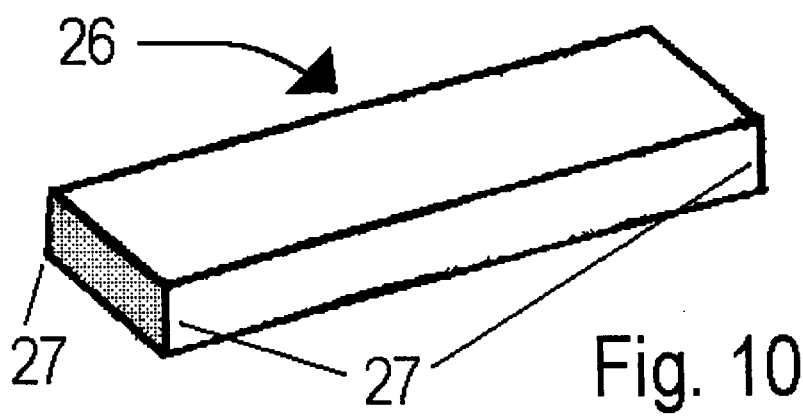
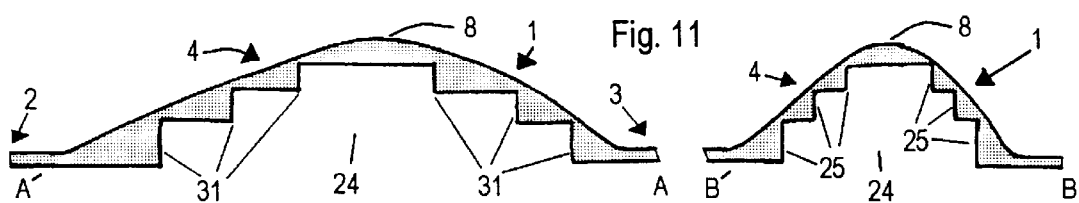

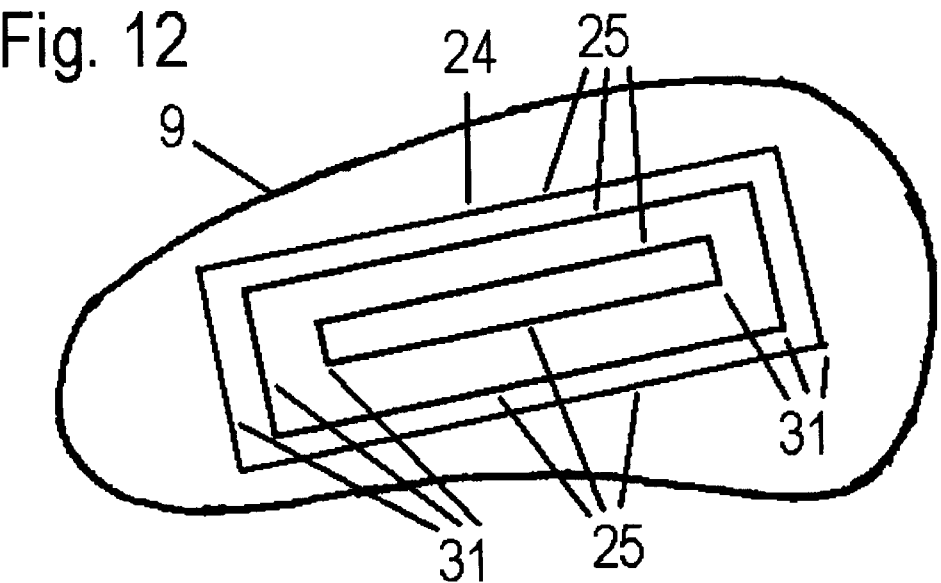
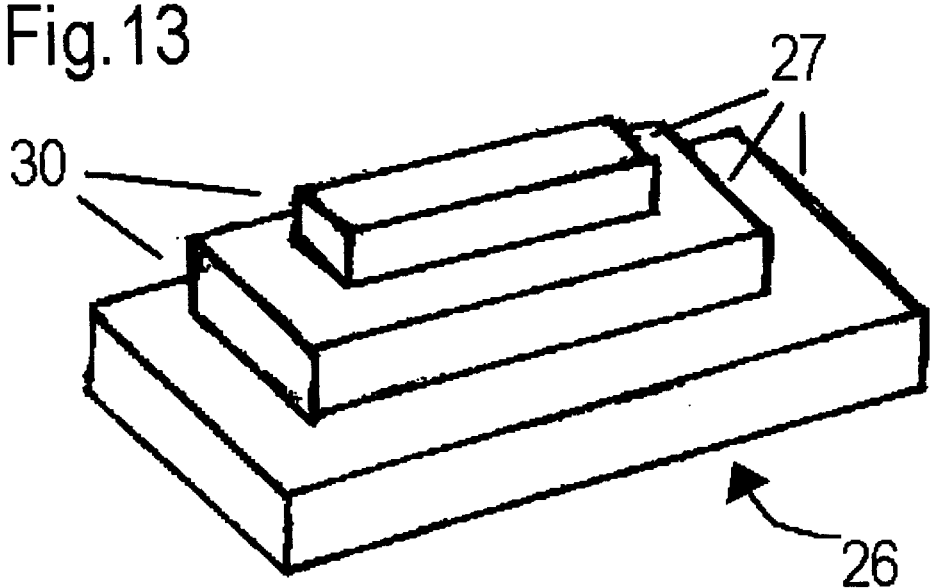
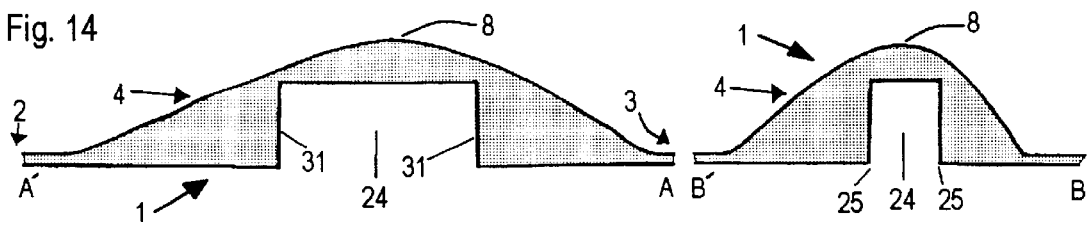

REHABILITATIVE SHOE INSOLE DEVICE

This application is a continuation-in-part of U.S. Pat. application No. 08/994,500 filed Dec. 24, 1997 now abandoned.

FIELD OF THE INVENTION

The present invention relates to an insole for a shoe. In particular, the present invention relates to an insole device that can rehabilitate a foot by stimulating a proprioceptive response in the wearer's foot.

BACKGROUND OF THE INVENTION

Professionals dealing with gait related pathologies generally accept that a large majority of persons will, at some time in their lives, suffer some form of gait related pain or dysfunction. It is well accepted that, in the majority of case, the mechanism underlying the pathology, injury, or dysfunction is biomechanically related to the interface between the foot and the ground, during the support phase of the gait cycle.

It has been proposed that providing a device to create a proprioceptive, or internal, feedback stimulus to a wearer's foot can directly target the underlying pathology, injury or dysfunction. Such a device is disclosed in U.S. Pat. No. 5,404,659 to Burk et al. As disclosed in U.S. Pat. No. 5,404,659, an arch rehabilitative catalyst stimulates the Golgi tendon organ, which in turn, stimulates the musculoskeletal structure of the foot to rehabilitate the foot structure. The catalyst is an asymmetrically domed hump, which creates a mild to strong discomfort to initially stimulate the Golgi tendon organ.

However, it has been found that the device disclosed in U.S. Pat. No. 5,404,659 does not function as described, and that the majority of wearers find the device too uncomfortable to use. In particular, when subjected to conventional vertical compressive forces of a person walking in the range of 2.5 times body weight, the device is designed to deflect between 40% and 60% of its maximum height, and when subject to only one times a person's weight, there should be no deflection. Rather than stimulate the Golgi tendon organ to create a proprioceptive response, deflections in this range can cause sever pain to a wearer, as there is insufficient give, and the wearer is always aware of the presence of the device. In addition, as disclosed in U.S. Pat. No. 5,504,659, the device has an ideal apex height of 5.25% to 7.6% of the total foot length. A device build according to these dimensions results in an overly high arch height, and can cause severe discomfort, and possible injury, to a wearer. It is further disclosed that the absolute, non-weight bearing height of the device should be the same regardless of body weight and arch height. This is clearly wrong, since different wearers will have different comfort thresholds and arch heights.

In general, the device disclosed in U.S. Pat. No. 5,404,659 does not function as described. Wearers would find the device too hard to use successfully, and rather than stimulating a proprioceptive response, the device would cause pain and discomfort at each step. The pain engendered in the foot of a wearer would, in fact, cause the wearer to limit the pressure applied to the foot to avoid the discomfort, rather than exercising the foot by creating an imperceptible stimulation as it is stated goal.

SUMMARY OF THE INVENTION

The present invention provides a shoe insole or midsole units that utilize proprioceptive feedback mechanisms in the human body to increase the structural integrity of the human foot. The improvements will introduce provisions allowing the arch rehabilitative catalyst to be consistently located at the desired anatomical location as well as to ease the interaction of the arch rehabilitative catalyst and the wearer. Improvements will also be presented to provide an increased longevity of the arch rehabilitative catalyst, as well to provide a gradual multi-directional interfacing with the arch rehabilitative catalyst.

According to one aspect of the invention there is provided an improved arch rehabilitative catalyst. In another aspect of the invention there is provided an improved ease of interchanging of the arch rehabilitative catalyst. In another aspect of the invention there is provided designs and systems which improve the longevity of the rebound, deflection and compression characteristics of the arch rehabilitative catalyst by introducing a mechanical device. In another aspect of the invention there is provided an improved mechanism allowing gradual multi-directional introduction of the arch rehabilitative catalyst to the plantar aspect of the foot.

According to other aspects of the invention there are provided a number of designs for maintaining the proper location of the arch rehabilitative catalyst through the introduction of geometric cavities and matching insertable resilient members with the presence of vertical sidewall interaction. Provisions to the design of these geometric cavities and matching insertable devices will be shown as a system to allow for ease of inter-changing of the arch rehabilitative catalyst support.

According to yet another aspect of the invention there is provided a tapered heel skive allowing for medial to lateral, as well as anterior to posterior gradual body weight acceptance onto the arch rehabilitative catalyst to increase the comfort of the invention.

DESCRIPTION OF THE DRAWINGS

Preferred embodiments of the present invention will now be described, by way of example only, by reference to the attached drawings, in which:

FIG. 6 is a perspective view of another embodiment utilizing a domed shape coil spring device of the present invention showing an undercarriage and positioning apertures;

FIG. 7 is a frontal plane cross-sectional view of further embodiment of a domed shaped coil spring device of the present invention through section B–B' of FIG. 6;

FIGS. 8a and 8b are frontal and sagittal plane cross sectional views of the insole or midsole through sections A–A' and B–B ' of FIG. 2 showing the positioning of a rectangular receptacle cavity in the area of the arch rehabilitative catalyst, respectively;

FIG. 9 is a plantar aspect view of the arch rehabilitative catalyst and the rectangular receptacle cavity in the arch rehabilitative catalyst shown in FIGS. 8a and 8b;

FIG. 10 is a perspective view of an insert that can be inserted into the rectangular receptacle cavity in the arch rehabilitative catalyst;

FIGS. 11a and 11b are frontal and sagittal plane view of further embodiment of the insole or midsole through sections A–A' and B–B' of FIG. 2 showing the positioning of a rectangular pyramidal receptacle cavity in the arch rehabilitative catalyst;

FIG. 12 is a plantar aspect view of the arch rehabilitative catalyst and the rectangular pyramidal receptacle cavity in the arch rehabilitative catalyst shown in FIGS 11a and 11b;

FIG. 13 a perspective view of an insert that can be inserted into the rectangular pyramidal receptacle cavity in the arch rehabilitative catalyst;

FIGS. 14a and 14b are frontal and sagittal plane views of another embodiment of an insole through sections A–A' and b–B' showing the positioning of a rectangular receptacle cavity with curvilinear ends in the arch rehabilitative catalyst;

FIGS. 23a and 23 b are frontal and sagittal plane views of further embodiment of the insole or midsole of the invention through sections A–A' and B–B ' of FIG. 2 showing the positioning of a rectangular receptacle cavity in the arch rehabilitative catalyst with the cavity displaying a combination of vertical sidewalls and tapered sidewalls.

DETAILED DESCRIPTION

Figure 1:
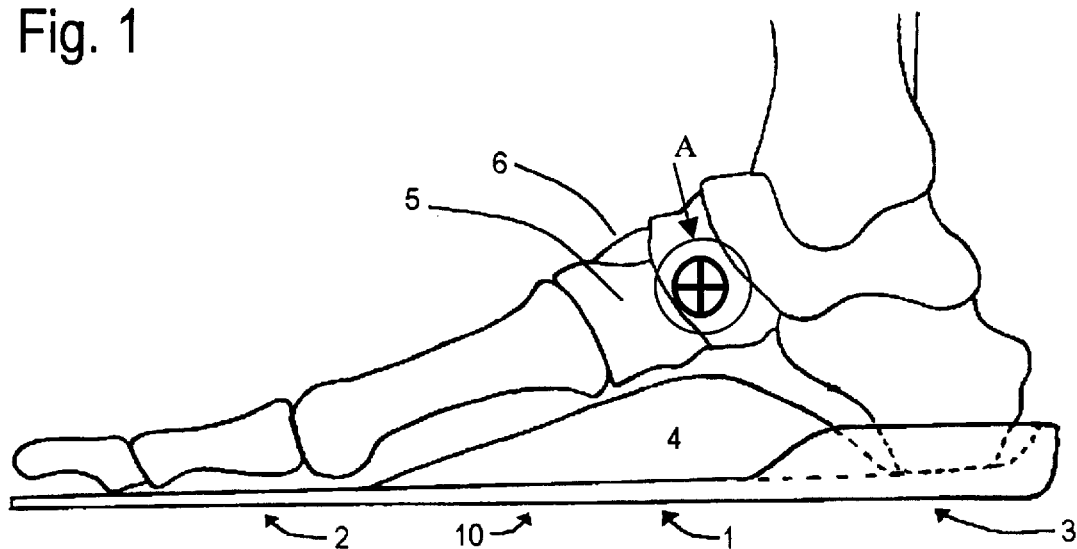
FIG. 1 is a medial sagittal view of an insole showing the location of an arch rehabilitative catalyst relative to foot placement on the insole or midsole.
Figure 2:
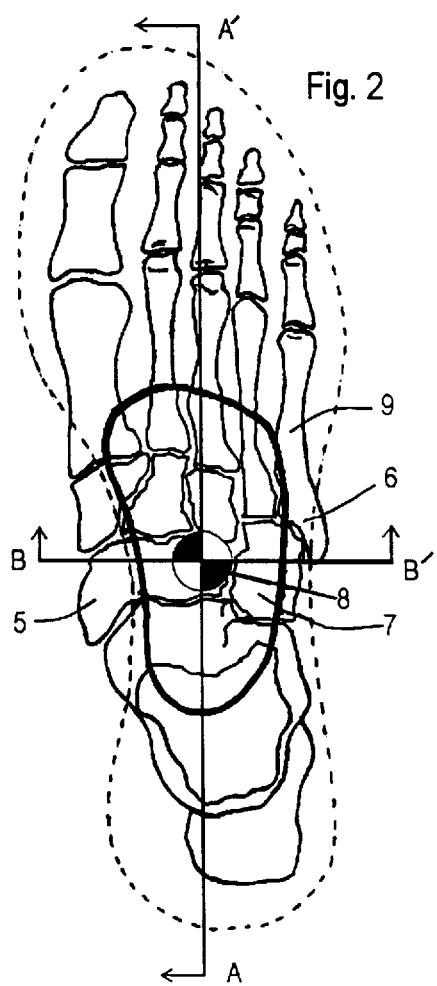
FIG. 2 is a dorsal view of an insole showing the location of an arch rehabilitative catalyst relative to foot placement.

Referring to FIGS. 1 and 2, an insole or midsole device 1 is shown. Device 1 has a dorsal surface contacting the underside of a foot. A proprioceptive catalyst 4 is located in the midsection of device 1, substantially aligned with the apex of the foot's arch system. The apex of the arch system is shown at the target area "A" shown in FIGS. 1 and 2, and is defined as the intersection of the navicular 5, lateral cuneiform 6, and the cuboid 7 bones, or slightly medial thereof. As will be understood by those of skill in the art, a wearer's foot comprises the bones of the foot, interconnected by ligaments. A layer of muscle is attached to the bones by tendons, and covered by a thick layer of fat tissue which is finally covered by a layer of skin.

The proprioceptive catalyst 4 has an area and perimeter 9 defined by an anterior arc, a posterior arc, a medial arc, and a lateral arc. Preferably, the anterior are has its maximum point lateral to the $2^{nd}$ metatarsal and medial to the $3^{rd}$ metatarsal, and does not extend in an anterior direction more that 70% of the total foot length, nor less than 60%; the posterior arc has its maximum point medial to the literal tubercle of the calcancus and lateral to the medial tubercle, and does not extent in a posterior direction at any point less that 15% of the foot's total length or greater that 25% of the foot's total length; the medial and lateral arcs do not exceed the medial and lateral boundaries created by the foot itself; and the proprioceptive catalyst 4 is entirely within the periphery set by the metatarsal heads, calcaneus, and lateral and medial borders of the foot.

Proprioceptive catalyst 4 is an asymmetric dome with its apex aligned with target area "A", as described above, when viewed from where a sagittal plane. The height the catalyst 4 at the apex should ensure that, when a user is at rest, target area "A" is at a height between 5.28% and 7.6% of the foot's total length. The present inventor has found that this corresponds to an actual catalyst height of in the range of 1% to 5% of the foot's length, with an ideal ration of approximately 3.6% of a wearer's foot length.

Preferably, catalyst 4 should be manufactured in such a fashion, and of such a material, that it displays certain preferred compression and rebound characteristics. For example, when the catalyst is subjected to the vertical forces of a person standing at rest, the catalyst will display a deflection between 40% and 100% of its maximum height.

Figure 3:
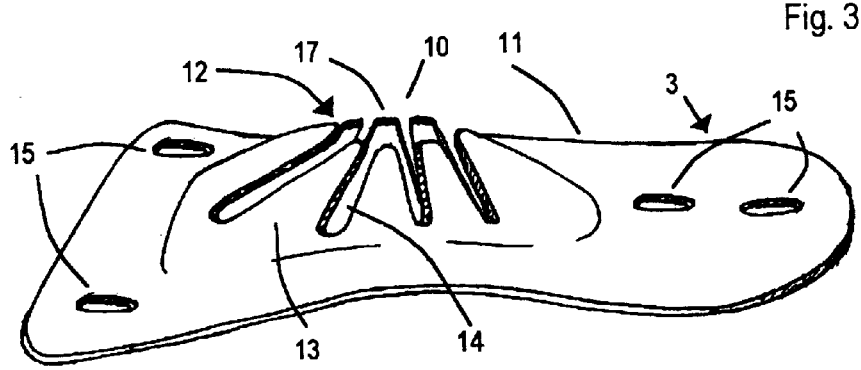
FIG. 3 is perspective view of a cantilever spring device of the present invention showing an undercarriage and positioning apertures.
Figure 4:
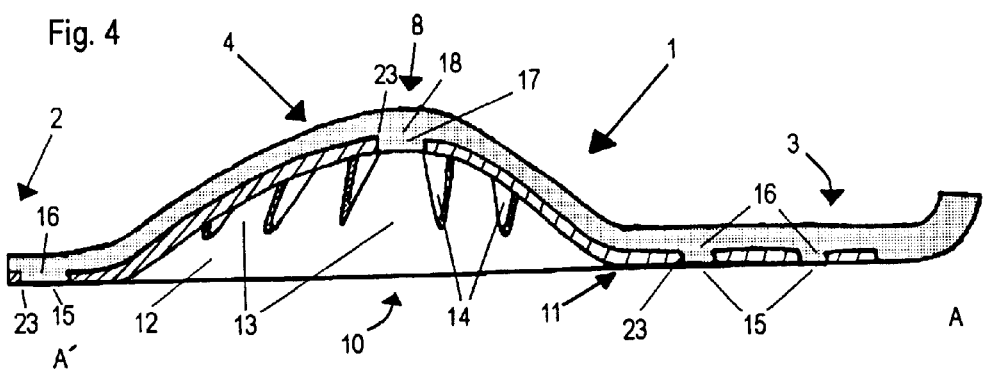
FIG. 4 is a sagittal plane cross-sectional view of the insole or midsole and the cantilever spring device of FIG. 3, through section A–A' of FIG.2.

A first embodiment of the present invention is shown in FIGS. 3 and 7. Referring to FIG. 3 and 4, the device 1 interfaces with an undercarriage 11 from a sagittal plane view through section A–A'. Undercarriage 11 has a heel region 3 and midfoot region 10. The midfoot region 10 defines a catalyst 4 supported by a resilient member in the form of a doomed cantilever spring device 12. Cantilever legs 13 flex and compress into voids 14, thereby allowing compression of the the legs 13 without the legs 13 interfering with each other during compression. The apex 8 of the catalyst, in the form of a cantilever spring device 12 provides a positioning aperture 17 aligned with a positioning pion 18 in the device 1. Positioning apertures 15 are also aligned with positioning pins 16 of the device 1 to ensure the proper placement and maintenance of placement of the catalyst 4 and its apex 8. Vertical side walls 23 of the positioning pins 16 and the positioning apertures 15 act to prevent anterior/posterior and medial/lateral shifting of the inserted mechanism as provided in FIGS. 3, 4, 5 and 6. The apertures 15 and corresponding placement pins 16 can be located at any location on the device 1 and the undercarriage 11 as seen fit by design and functionality. Differences in body weight, activity and foot type can be compensated for by the selection of materials for fabrication of the undercarriage 11 and the cantilever spring device 12, or the thickness of the undercarriage 11 and the cantilever spring device 12. The undercarriage 11 and the cantilever spring device 12 can be formed through injection moulding or vacuum forming and stamping. Polymers such as Delrin, Hytrel and Zytel from E.I. DuPont, PVC, Pebax or layered fabric and resin combinations such as fiberglass or graphite can provide the desired physical and material properties.

An advantage of device 1 is the high flex fatigue characteristics of the materials of choice. This will enable the device 1, and in particular the catalyst 4, to be used for much longer periods of time than that disclosed in other shoe insole or midsole units that utilize proprioceptive feedback mechanisms in the human body to increase the structural integrity of the human foot. The desire regulation of the vertical maximum distance from the supporting surface of the device 1 to the apex 8 of the catalyst 4 occurs as forces are applied vertically to the cantilever mechanism at is apex 8.

Figure 5:
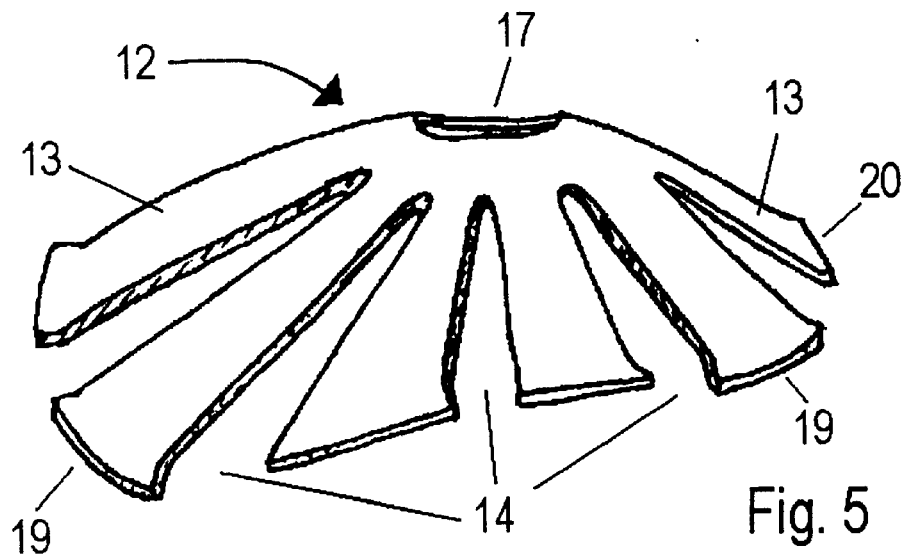
FIG. 5 is a perspective view of an alternative embodiment of the cantilever spring device of the present invention to be designed into the undercarriage.

FIG. 5 illustrates an alternative design to the cantilever spring device 12 where the legs 13 of the cantilever spring device 12 deflect and move away from the centre region. A rear finger 20 on the spring device 12 in FIG. 5 can be molded as an integral part of the undercarriage 11 or permanently affixed to an undercarriage 11. Each leg 13 of the cantilever spring device 12 has a foot 19 that permits it to smoothly elongate without becoming obstructed by friction between the lower surface of the foot 19 and the layer of the inside of the shoe with which ii is in contact. This embodiment as illustrate in FIG. 5, also incorporates positioning pins 18 and 16, and positioning apertures 15 and 17 and their inherent vertical sidewalls 23 to ensure the proper placement of the catalyst 4 and its apex 8 which maintains the catalyst in its position.

FIG. 6 shows a further configuration for the resilient member supporting catalyst 4 of the present invention. It involves the incorporation of a coiled spring device 21 to be aligned to the target area of the apex 8 of the foot's arch system as defined and to be affixed to or designed as an integral part of the undercarriage 11. This is illustrated in FIG. 6 where a perspective view of the coied spring device 21 is shown. Again the incorporation of positioning pins 16 and the positioning apertures 15 and the vertical sidewalls 23 created therein prevent any medial/lateral and anterior/posterior shifting of the mechanism and ensure its proper placement.

It is believed that the specific characteristics that are desired the cantilever spring mechanisms of the present invention can be attained in at least two different ways. The first of these is to use the design, particularly the design characteristics of the legs 13 as a constant, and adopt different grades of the aforementioned polymers, or similar. The calculation of the vertical force being applied and the use of trigonometry will allow the simple calculation of the force vector representing that going down the legs 13, and this can be used to determine the desired polymer, or grade of polymer, based on its flex modulus: F=(KX); where F is the force being applied vertically at the apex 8, K is the spring constant which can be provided through the flex modulus, and X is the distance that the spring changes in length, in this case the difference between the resting height "H+X" and the height "H" when the cantilever is compressed through the application of a vertical force applied at the target area.

The second method of attaining the desired rebound and compression characteristics would be to hold the polymer of choice as a constant and alter the thickness of the legs 13 as shown in FIGS. 3, 4 and 5. The use of the flex modulus information, relative to material thickness, will be able to provide the necessary information as to determine the ideal material thickness. The benefit of this, is its ability to provide a variable deflection rate. That is the cantilever mechanism 12 can be designed to react equally efficiently when subjected to varying forces through varying thickness of the legs 13. An example of which is the integration of thicker legs 13 if the application is such that it provides an activity or an environmental stress characteristic of greater vertical loading, such as the activity of basketball compared to walking, or 150 kg athlete compared to a 80 kg athlete, both having the same shoe size.

The benefits of the improved rehabilitative catalyst of the present invention are generally threefold. First, the position pins 16 and the positioning apertures 15 and their complimentary vertical sidewalls 23 ensure the proper placement of the catalyst 4 and the maintenance of the placement. Second, by properly integrating a resilient member with the polymers and materials of choice as discussed, the catalyst is capable of showing extremely high durability characteristics. Third, the resilient member can be designed to obtain the desired compression and spring characteristics required for a particular application. The maintenance of these properties is benefical because:

I) The rebound characterisitics ensure that the catalyst 4 will return to its original apex height 8, thereby ensuring contact with the apex of the foot's arch system. This contact provides a catalyst to stimulate the proprioceptive mechanism necessary for the proper restructuring of the foot's arch systems' musculosketal characteristics.

II) The compression characteristics allow the human foot's arch system to deflect in a natural manner and thereby the human arch system an act as a natural cushioning mechanism. This also prevents any bracing effects from occurring.

III) The compression characteristics allow the human foot arch system to deflect in a natural manner thereby allowing eccentric contractions of the foot's plantar musculature to occur. This regulates the velocity of arch deflection as well as allows the series and parallel spring characteristics of the muscle to store energy and contribute that stored energy to effective propulsion.

In another aspect of the invention it is desirable to redesign the geometric nature of the plantar aspect of the device 1 in the region of the catalyst 4 to facilitate the easy removal and insertion of an appropriately shaped resilient member 26, as per a few of the options presented in FIGS. 10, 13, 16, and 17, to provide the necessary rebound, compression and deflection traits necessitated by the wearer and to provide vertical walls 25 and 31 thereby ensuring proper positioning of the resilient member 26 and catalyst and to ensure the proper maintenance of the desired position. The insertable resilient member 26 allows for customization of the catalyst in the same manner as discussed with reference to the legs 13 of the spring device. The resilient member 26 can be provided in a variety of foam type materials of a variety of heights, hardnessess and compression sets to address body weight requirements, foot type characteristics, or activity of usage.

Previous inventions have featured a catalyst having a receptacle in the form of a cavity having no vertical walls to ensure proper positioning of the filler object or insert 26 or mechanism and to ensure the proper maintenance of the desired position.

The removal and insertion of resilient members into the aforementioned curvilinear cavity has revealed two shortcomings, the first of these was that when a lower strength adhesive system was used that facilitated the ease of removal and insertion of the resilient member the resilient member was predisposed to shift out of position when subjected to the medial/lateral shearing forces that are characteristic of normal gait. This shifting prevented the resilient member from being maintained in the desired position as outlined.

The second shortcoming was evident when an adhesive system of adequate strength was used to ensure the positional maintenance of the resilient member. The adhesives used proved to display tensile strength properties far in excess of the surrounding devide 1 material and the resilient member. Attempts to dislodge the resilient member for the purpose of inserting a newer resilient member as necessitated by the foot re-structuring initiated by the invention, proved to cause substantial damage to the device 1 material to the extent rendering the device 1 unusable.

FIGS. 8 through 19 reveal options that are available with respect to the redesign of a system that ensures the proper placement of the resislient member 26, the maintenance of that placement and the easy removal and insertion of the resilient member 26.

FIGS. 8 thorugh 10 reveal an device 1, with a forefoot region 2, a heel region 3 and with an catalyst 4 with a distinct apex 8, the target area aligned with the anatomical region encompassing the intersection of the navicular 5, lateral cuneiform 6, and the cuboid 7 bones. The plantar surface of the device 1 in the region set forth by the boundaries of the caralyst 4 is charcterized by a geometric cavity 24. The cavity displays vertical walls 25 for resisting medial-lateral shifting of the resilient member 26 and vertical walls 31 for resisting anterior-posterior shifting of the rsilient member 26. The preferred embodiment as detailed in FIGS. 8 through 10 reveal a geometric cavity 24 of a rectangular nature and a resilient member 26 of a corresponding rectangular nature with vertical side walls 27 designed to engage with the vertical sidewalls 25 and 31 of the cavity 24.

FIGS. 11 through 13 show a device 1, with a forefoot region 2, a heel region 3 and with a catalyst 4 with an apex 8, the apex aligned witha target area in the foot defined by the anatomical region encompassing the intersection of the navicular 5, lateral cuneiform 6, and the cuboid 7 bones. The plantar surface of the deive 1 in the region set forth by the boundaries of the catalyst 4 is characterized by a geometric cavity 24. The cavity displays vertical walls 25 for engaging with vertical sidewalls 27 of the resilient member 26 for resisting medial-lateral shifting of the filler resilient member 26 and vertical walls 31 for engaging with the vertical sidewalls 27 of the resilient member 26 for resisting anterior-posterior shifting of the resilient member 26. The preferred embodiment as detailed in FIGS. 11 through 13 reveals a geometric cavity 24 of a pyramidal stacked rectangular nature and a resilient member 26 of a corresponding pyramidal stacked rectangular nature. In reference to this configuration it is possible to have the rectangular layers 30 each as an insatiable filler object or insert layer and therefore each of a different material and/or differing material properties. In this manner the variable rate deflection concept outlined earlier can be attained while maintaining and ensuring the proper positioning of the catalyst 4, apex 8 and the resilient member 26. This variable deflection benefit an also be achieved through the method as provided in FIGS. 8 through 10 by allowing the resilient member 26 to be constructed through the application of stacked layers where each layer is capable of displaying individual deflection, compression and reboudn characteristics.

Figure 15:
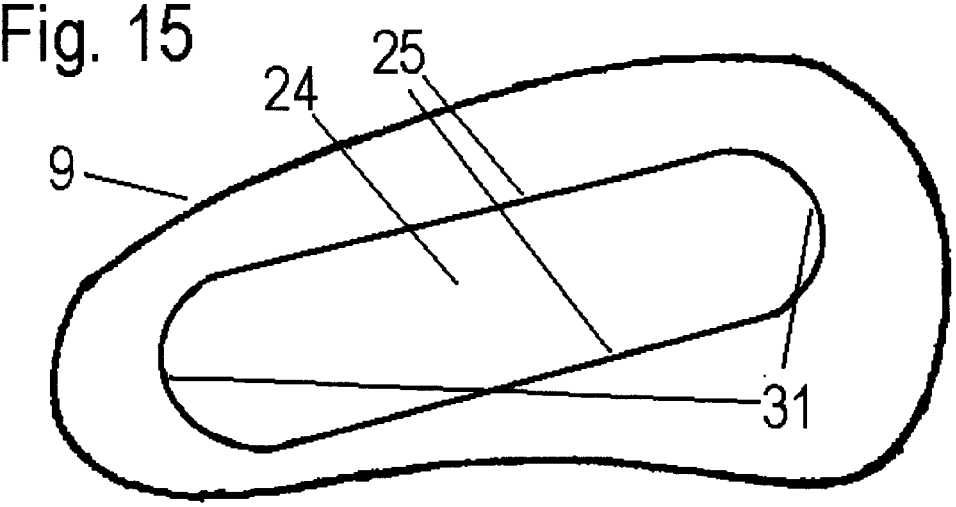
FIG. 15 a plantar aspect view of the arch rehabilitative catalyst and the rectangular receptacle cavity with curvilinear ends in the arch rehabilitative catalyst shown in FIGS. 14a and 14b.
Figure 16:
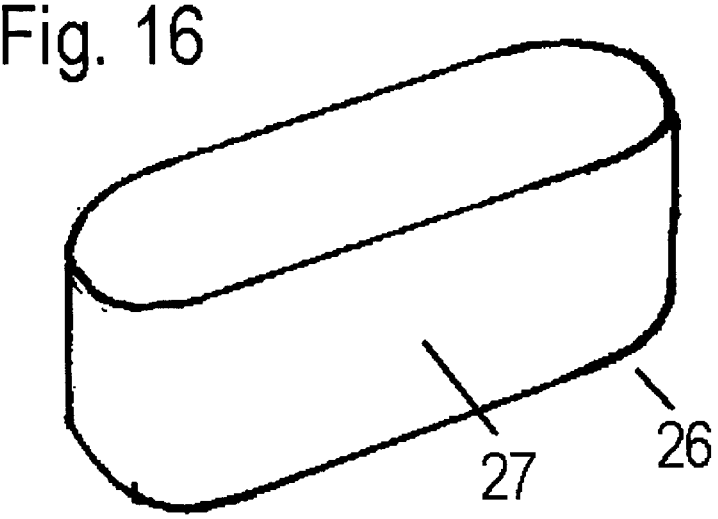
FIG. 16 is a perspective view of an insert that can be inserted into the rectangular receptacle cavity with curvilinear ends in the arch rehabilitative catalyst shown in FIGS. 14a and 14 b.

FIGS. 14 through 16 display a geometric configuration consistent with FIGS. 8 through 10 with the exception of the anterior and posterior most ends of the resilient member 26, and the anterior and posterior walls of the geometric cavity 24, are curvilinear in nature.

The geometric cavity 24 can also be designed to facilitate the insertion of an appropriately matching shaped resilient member other than of foam type material providing the desired rebound, deflection and rebound characteristics. The resilient member can take the form of a compressive mechanical system such as coil spring devices, bi-value spring devices, cantilever spring devices, or fluid filled structures, including gas filled structures. The resilient member is designed to fill the geometric cavity such that the vertical sidewalls 25 and 31 of the geometric cavity 24 engage the resilient member and ensure the proper permanent placement of the resilient member. The compressive nature of the resilient member can be linear in nature or can provide a vaiable rate of deflection.

Figure 17:
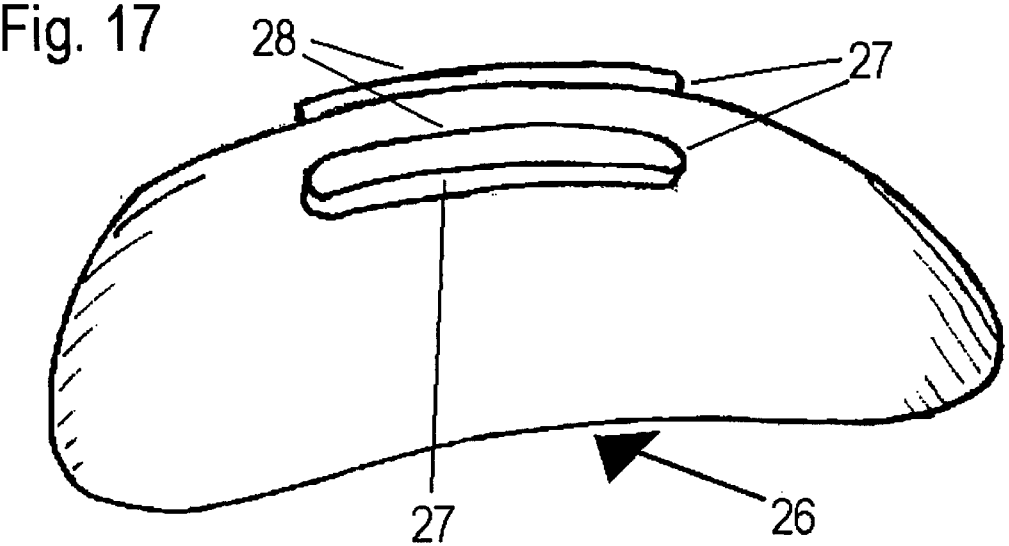
FIG. 17 a perspective view of further embodiment of a domed shaped insert with positioning and security ribs on its dorsal aspect.
Figure 18:
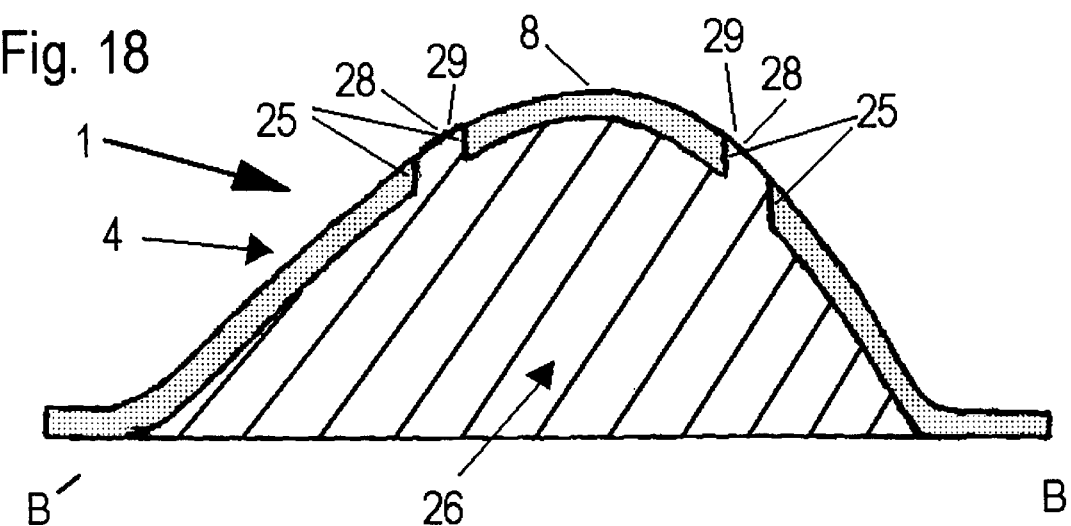
FIG. 18 is a frontal cross-sectional view of the arch rehabilitative catalyst and insole or midsole through section B–B' of FIG. 2 showing the domed shaped insert with 2 positioning and security ribs of FIG. 17.
Figure 19:
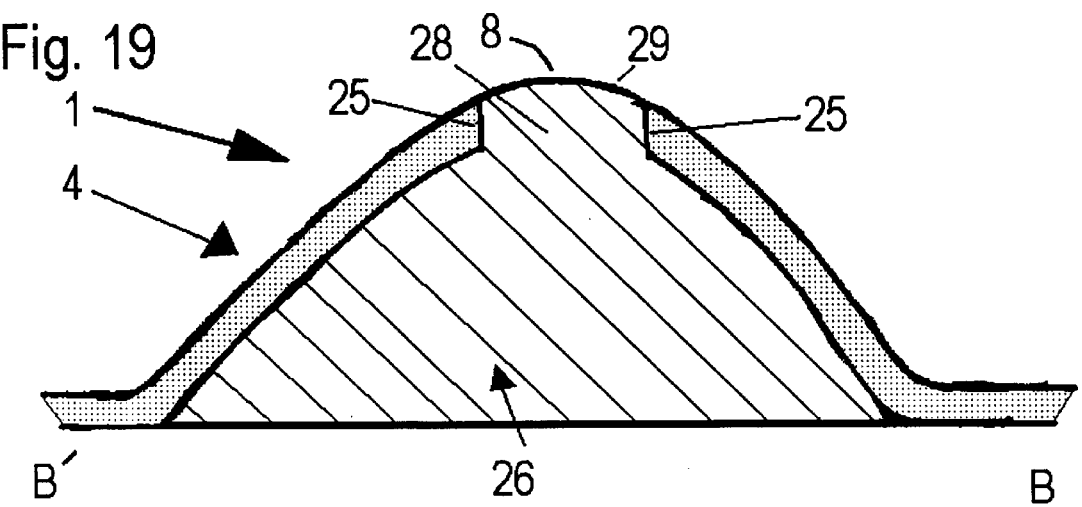
FIG. 19 a frontal cross-sectional view of another embodiment of a arch rehabilitative catalyst and insole or midsole through section B–B' of FIG. 2 showing the domed shaped insert with a singular positioning and security rib.

FIGS. 17 through 19 illustrate a mechanism allowing a resilient member 26 of similar shape and design as the curvilinear geometric cavity 24 to be inserted into the curvilinear geometric cavity 24 without risk of the resilient member 26 deviating from its desired position. In this aspect of the disclosure apertures 29 are present in the catalyst 4 area of the device 1 which are aligned to receive positiongin and security ribs 28 designed as an integral characteristic of the resilient member 26. The positioning and security ribs 28 have vertical sidewalls 27 which engage with the vertical sidewalls 25 an 31 of the insole or midsole to prevent any medial-lateral shifting or posterior-anterior shifting of the position of the resilient member 26.

Figure 23:
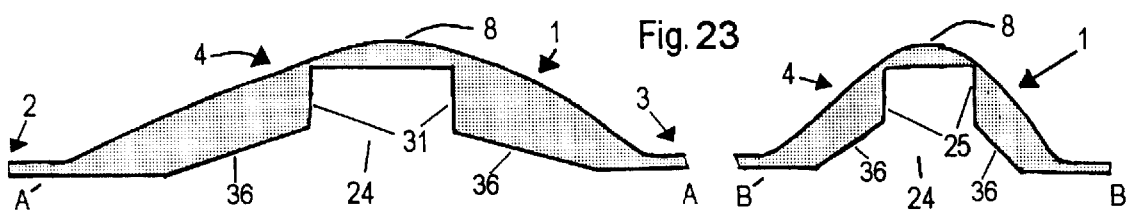

FIG. 23 reveals a preferred method of ensuring the presence of vertical sidewalls 31 and 25 in the geometric cavity 24 necessary to secure the resilient member 26 and providing an intrinsic cantilever effect. Vertical sidewalls 31 and 25 extend vertically downwardly from a maximum height, a predetermined distance, such that the distance is less than the maximum vertical distance from the inside maximum height of the geometric cavity 24 and the plantar supporting surface of the insole 1. The lower portion of the geometric cavity 24 is characterized by sidewalls 36 that are tapered. This design further utilizes the material properties of the insole body to provide a futher cantilevler effect as well as allowing a pumping action upon compression capable of circulating air throughout the in-shoe environment.

Figure 20:
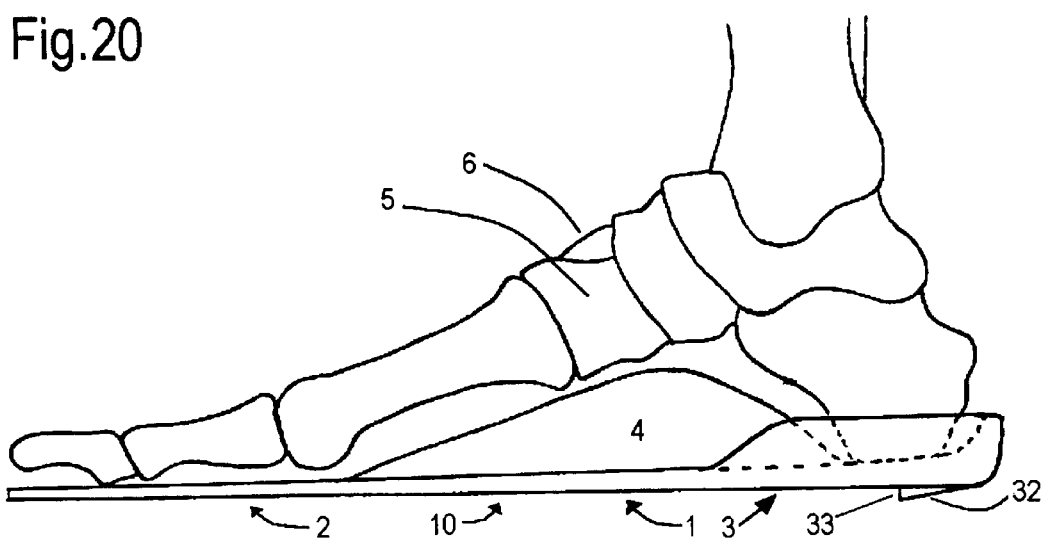
FIG. 20 a medial sagittal view of another embodiment the invention showing the location of the arch rehabilitative catalyst relative to foot placement on the insole or midsole and the posterior heel skive.
Figure 21:
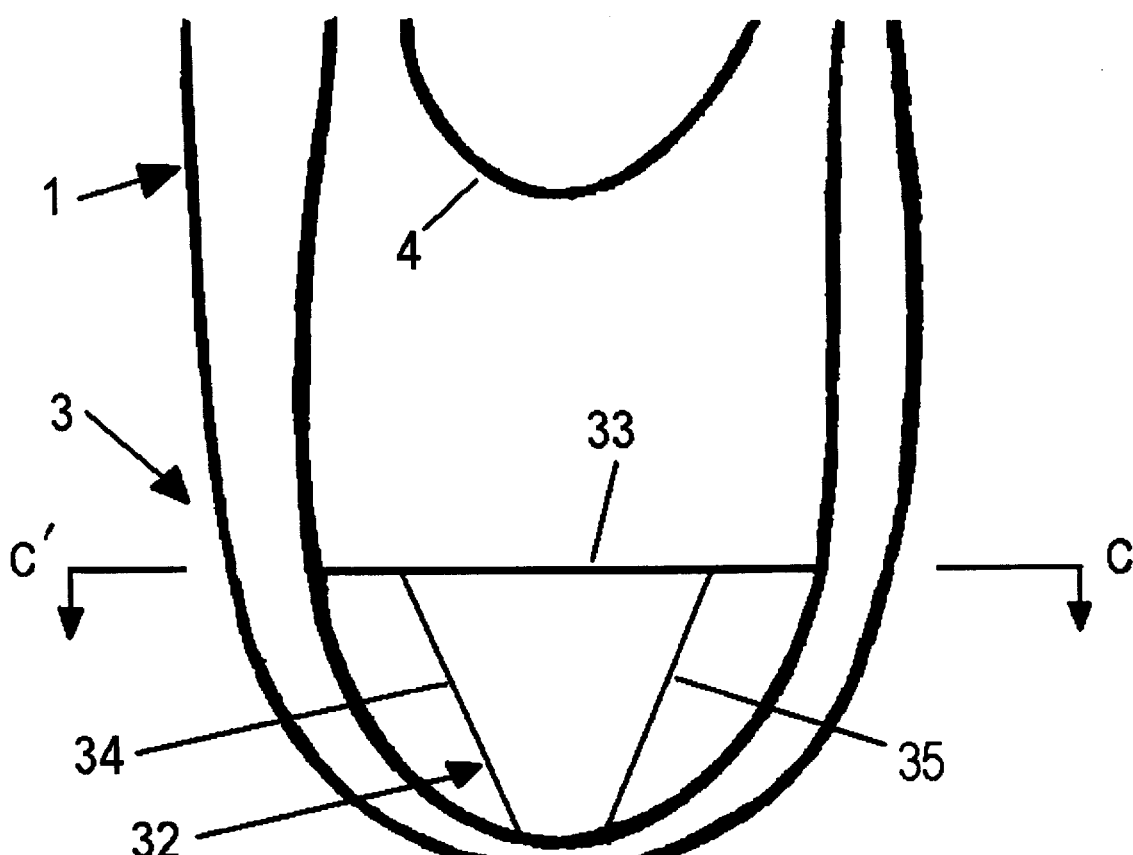
FIG. 21 view of the heel region of the insole or midsole device illustrating the location and characteristics of the tapered heel skive as shown in FIG. 20.
Figure 22:
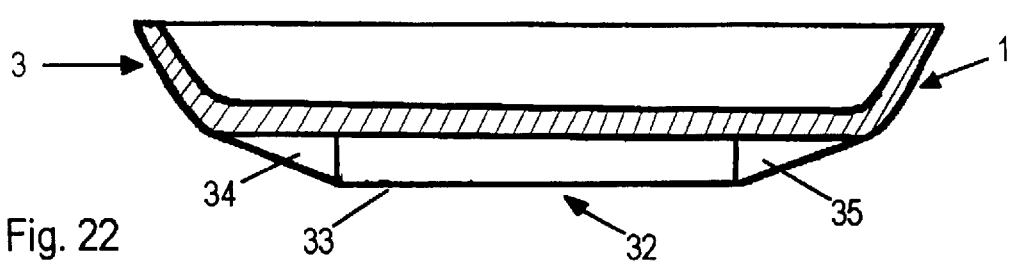
FIG. 22 a frontal plane cross sectional view through section C–C' of FIG. 21 showing the geometric characteristics of the posterior heel skive.

In another aspect of the invention, device 1 as described, has a heel region 3 comprised of a tapered skive 32, as shown in FIG. 20, wherein the maximum skive thickness corresponds with the sagittal plane midline of the calaneus and tapers by means of a sagittal angle to a level equal to the maximum thickness of the device 1 at the posterior most part of the device 1.

In this the tapered 32 serves to reduce the velocity of the foot once it is planted on the ground at heal strike in normal heel to toe ambulation. This functions as a precaution by allowing the foot to be slowly lowered unto the catalyst 4. In doing so, any risk of impact related injury to the foots arch system is reduced as well as increasing the intial comfort of the device 1 by allowing the pressure application to be more gradual.

The tapered skive provided for in other inventions are sufficiently able to perform effectively during an uni-directional ambulation but was designed such that it was not very effective in reducing the impact velocity when the foot was planted medially or laterally as in multi-directional sports. The purpose of slowly lowering the foot onto the catalyst 4 is still maintained during uni-directional ambulation through the sagittal plane taper created by the slope existing from the anterior most edge 33 and the posterior most edge of the device 1, and this effect can now also be provided for when the insole or midsole device 1 is used in multi-directional sports by the design addition of the medial skive 34 and the lateral skive 35. Again this serves to function as a precaution by allowing the foot to be slowly lowered unto the catalyst 4. In doing so, any risk of impact related injury to the foot's arch system is reduced, as well as increasing the initial comfort of the insole or midsole 1 by allowing the pressure application to be more gradual. A non-symmetric altering of the medial and lateral skive 34 and 35 such that their angulations are different can be desirable for the design and creation of sport specific insole or midsoles.

It is understood that the above embodiments are illustrative of the invention and can be varied or amended with departing from the scope of the invention as defined in the appended claims.

What is claimed is:

1. A rehabilitative insole device in combination with a resilient member comprising:

a substantially dome shaped catalyst for interfacing with the plantar aspect of a human foot;

said catalyst having an apex for aligning with a target area within said foot, said target area defined by the point of articulation of the lateral cuneiform, cuboid and navicular bones of the foot, to permit uninhibited tri-planar pivoting of the foot about the target area;

said catalyst having a maximum height at said apex of from 1% to 5% of the length of said foot, wherein the length of said foot corresponds substantially to the length of said rehabilitative insole device;

said catalyst has a receptacle for removably accommodating said resilient member for causing said catalyst to apply an upwardly directed pressure to stimulate the Golgi tendon organ in said foot in response to downward pressure on said catalyst by said foot;

said receptacle in said catalyst includes vertical walls for interfacing with corresponding vertical walls on said resilient member to resist lateral shifting therebetween; and, said resilient member permits said catalyst to deflect from between 40% and 100% of said maximum height in response to a vertical forces of a person standing at rest being applied to said catalyst.

2. A rehabilitative insole device as claimed in claim 1 wherein:

said receptacle has an outwardly tapered side wall portion between said vertical walls and a plantar surface of said insole.

3. A rehabilitative insole device as claimed in claim 1 further comprising:

a tapered skive in a heel region thereof having a maximum skive thickness corresponding with a sagittal plane midline of the calcaneus and tapering by means of a sagittal angle to a level equal to the minimum thickness of said device at the posteriormost part of said device.

4. A rehabilitative insole device in combination with a resilient member as claimed in claim 1 further comprising:

a tapered skive in a heel region thereof having a maximum skive thickness corresponding with a sagittal plane midline of the calcaneus and tapering by means of a sagittal angle to a level equal to the minimum thickness of said device at the posteriormost part of said device;

said tapered skive further including a medial skive and a lateral skive.

5. A rehabilitative insole device in combination with a resilient member as claimed in claim 4 wherein:

said catalyst has a maximum height at said apex of about 3.6% of the length of said foot.

6. A rehabilitative insole device in combination with a resilient member as claimed in claim 1 wherein:

said resilient member is a member selected from the group consisting of a cantilever spring, a coil spring, and a bi-valve spring and further includes at least one positioning aperture having said vertical walls.

7. A rehabilitative insole device in combination with a resilient member as claimed in claim 6 wherein:

said catalyst has a maximum height at said apex of about 3.6% of the length of said foot.

8. A new rehabilitative insole device in combination with a resilient member as claimed in claim 1 wherein:

said resilient member is a foam type material.

9. A rehabilitative insole device in combination with a resilient member as claimed in claim 8 wherein:

said cavity and said insert have corresponding curvilinear ends.

10. A rehabilitative insole device in combination with a resilient member as claimed in claim 9 wherein:

said catalyst has a maximum height at said apex of about 3.6% of the length of said foot.

11. A rehabilitative insole device in combination with a resilient member as claimed in claim 8 wherein:

said catalyst has a maximum height at said apex of about 3.6% of the length of said foot.

12. A rehabilitative insole device in combination with a resilient member as claimed in claim 1 wherein:

said resilient member is a member selected from the group consisting of gas filled and fluid filled structures.

13. A rehabilitative insole device in combination with a resilient member as claimed in claim 12 wherein:

said catalyst has a maximum height at said apex of about 3.6% of the length of said foot.

14. A rehabilitative insole device in combination with a resilient member as claimed in claim 1 wherein:

said catalyst has a maximum height at said apex of about 3.6% of the length of said foot.

15. A rehabilitative insole device as claimed in claim 1 wherein:

said catalyst has a maximum height at said apex of about 3.6% of the length of said foot.

* * * * *